US008940336B2

(12) United States Patent
Alexander et al.

(10) Patent No.: US 8,940,336 B2
(45) Date of Patent: Jan. 27, 2015

(54) POLYMER PARTICLES PREPARED FROM POLYMERISABLE ALKYLENE GLYCOL (METH) ACRYLATE MONOMERS (75) Inventors: Cameron Alexander, Nottingham (GB); Kevin Shakesheff, Nottingham (GB); Liang He, Aberdeen (GB); Martyn Davies, Nottingham (GB); Wenxin Wang, Nottingham (GB); Brian Saunders, Manchester (GB)

(73) Assignee: University of Nottingham, Nottingham (GB)

( * ) Notice: Subject to any disclaimer, the term of this patent is extended or adjusted under 35 U.S.C. 154(b) by 92 days.

(21) Appl. No.: 13/123,737

(22) PCT Filed: Oct. 13, 2009

(86) PCT No.: PCT/GB2009/051362
§ 371 (c)(1),
(2), (4) Date: Aug. 29, 2011

(87) PCT Pub. No.: WO2010/043892
PCT Pub. Date: Apr. 22, 2010

(65) Prior Publication Data
US 2011/0305767 A1    Dec. 15, 2011

(30) Foreign Application Priority Data

Oct. 13, 2008 (GB) .................................... 0818747.8

(51) Int. Cl.
*A61K 9/50* (2006.01)
*A61K 9/14* (2006.01)
(Continued)

(52) U.S. Cl.
CPC ............ *C12N 5/0068* (2013.01); *C12M 25/14* (2013.01); *C12N 2533/40* (2013.01);
(Continued)

(58) Field of Classification Search
None
See application file for complete search history.

(56) References Cited

U.S. PATENT DOCUMENTS

| | | | |
|---|---|---|---|
| 6,103,528 A | 8/2000 | An et al. | 435/395 |
| 2004/0195710 A1 | 10/2004 | Hubbell et al. | 264/4.1 |
| 2006/0116290 A1* | 6/2006 | Heming et al. | 504/360 |

FOREIGN PATENT DOCUMENTS

| | | |
|---|---|---|
| EP | 0 373 626 | 12/1989 |
| JP | 62224290 A * | 10/1987 |

(Continued)

OTHER PUBLICATIONS

Mougin et al., Towards a self-assembled membrane made of bionanoparticle-polymer conjugates, The 236th ACS National Meeting, Philadelphia, PA, Aug. 2008, accessed online at www.chemie.uni-bayreuth.de/mcii/en/pub/pub/32087/307.pdf.*

(Continued)

*Primary Examiner* — Carlos Azpuru
*Assistant Examiner* — Casey Hagopian
(74) *Attorney, Agent, or Firm* — MacCord Mason PLLC (57) ABSTRACT The invention provides polymer particles that are obtainable by a method selected from emulsion methods, diffusion methods and evaporation methods carried out in the presence of surface-engineering surfactant which is one or more polymer that displays a lower critical solution temperature, in aqueous media, that is between 10 to 90° C., this polymer being the polymerization product of one or more monomer selected from polymerisable alkyleneglycol acrylate monomers and polymerisable alkyleneglycol methacrylate monomers. The polymer particles can be used in controlled release applications, such as flavour release applications, fragrance release applications and biomedical applications. The invention also provides a cell support matrix comprising the polymer particles.

21 Claims, 7 Drawing Sheets (51) Int. Cl.
   *C12N 5/00*     (2006.01)
   *C12M 1/12*     (2006.01)
   *C08F 220/28*   (2006.01)

(52) U.S. Cl.
   CPC ....... *C12N 2539/10* (2013.01); *C08F 2220/286* (2013.01); *C08F 2220/287* (2013.01)
   USPC ............ 424/497; 424/489; 424/484; 424/486

(56) References Cited

FOREIGN PATENT DOCUMENTS

| JP | 2005213428 | 8/2005 | |
| JP | 2004-501993 | 7/2011 | ............. C12P 21/00 |
| WO | WO2004/087228 | 10/2004 | ............. A61L 15/24 |
| WO | WO2007069272 | 6/2007 | ............. A61K 45/08 |

OTHER PUBLICATIONS

Pich et al., Preparation of PEGMA-functionalized latex particles. 2. System styrene-N-vinylcaprolactam, Colloid Polym Sci (2003) 281: 916-920.*
Heath et al; Varying Polymer Architecture to Deliver Drugs; The AAPS Journal, 2007, pp. 235-240.
Hoogenboom et al; Synthesis and Screening of Polymer Libraries for Lost Behavior and Mechanical Properties; Polymer Preprints 2007 48(1), pp. 177-178.
Fraylich et al., Poly(D,L-lactide-co-glycolide) Dispersions Containing Pluronics: from Particle Preparation to Temperature-Triggered Aggregation; Langmuir 2008, 24, pp. 7761-7768.
Wang et al; Biodegradable Thermoresponsive Microparticle Dispersions for Injectable Cell Delivery Prepared Using a Single-Step Process; Advanced Materials 2009, 21, 1809-1813.
European search report from counterpart application; Aug. 3, 2012, 6pgs.

* cited by examiner

POLYMER PARTICLES PREPARED FROM POLYMERISABLE ALKYLENE GLYCOL (METH) ACRYLATE MONOMERS

This application is a 371 of PCT/GB2009/051362 filed 13 Oct. 2009, which claims priority of GB 0818747.8 filed 13 Oct. 2008.

The present invention relates to stabilised polymer particles, and their use in controlled release applications. The polymer particles may be used in cell delivery, for example the polymer particles may be used as cell support matrices. The stable polymer particles are prepared using LCST polymers. These LCST polymers (polymer that displays a lower critical solution temperature (LCST) in aqueous media that is between 10 to 90° C.) and processes for their production are also described.

The emerging field of regenerative medicine is reliant on materials that combine the ability to deliver cells to a target site and to support cell growth while maintaining ease of use in a clinical setting. Direct injection of cell suspensions to the body without a carrier is inefficient, compromises the viability of the cells and generates poor starting conditions for tissue regeneration.

Cell delivery materials are required that can be formulated with cells at room temperature but which, when co-injected with the cells into the body, can aggregate in situ into a porous gel that will protect the cells and subsequently promote tissue growth.

Thermoresponsive polymers (i.e. materials that undergo conformational or phase changes in response to a heat stimulus) have attracted particular attention for tissue engineering applications, because many such polymers are now available that undergo a phase transition close to 37° C. Poly(N-isopropylacrylamide) (PNIPAm) has been the most widely studied polymer of this class, but is not currently FDA approved for clinical applications.

Certain poly(ethylene oxide)-co-poly(propylene oxide) (PEO-PPO) co-polymers exhibit reverse thermal gelation behaviour in water, forming semi-solid gels when heated above their Lower Critical Solution Temperature (LCST) and are used in the pharmaceutical industry because the base polymers PEO and PPO are biocompatible. Other materials that exhibit this behaviour include poly(caprolactone) (PCL) and poly(lactide)-(PLA) block co-polymers (e.g. PEO-PCL-PEO).

However, the gels formed by these polymers are either too mechanically unstable to be used for cell scaffolds/cell delivery, or the concentrations required to form stable gels on introduction into the body are too high for practical use.

An attempt to overcome these problems is by preparing micelle-forming polymers with a cross-linkable core or shell, as in Joralemon et al, Journal of the American Chemical Society, 127, 16892-16899 (2005).

It is also possible for stable particles to be generated with a responsive surface, but these are synthetically demanding, or require monomers or cross-linkers that are not considered toxicologically acceptable. See, for example, Hales et al, Langmuir 20, 10809-10817 (2004); Fujii et al, Journal of the American Chemical Society 127, 7304-7305 (2005); and Pilon et al, Langmuir 21, 3808-3813 (2005).

Self-assembling aggregates with thermoresponsive polymers at the surface have been prepared from silica and from gold particles. See Zhang et al, Macromolecules 38, 9813-9820 (2005); and Kim, D. J. et al., Macromolecular Chemistry and Physics 206, 1941-1946 (2005).

However, to date, there have been no reports wherein biocompatible thermoresponsive polymers have been surface-engineered into forming biodegradable particles to generate porous cell-polymer composite gels.

In the present invention there are provided new surface-engineered 'smart' microparticles that can be prepared in a facile manner, which disperse with cells at temperatures below 37° C. to form free-flowing suspensions, and which form space-filling gels at body temperature that support cell growth. The microparticles include novel biocompatible thermoresponsive polymers. These polymers are designed such that they can partition into the surface of biodegradable polymer spheres during particle preparation, thus generating microparticles having highly controllable colloidal stability and biomaterial properties in a simple, single step procedure.

The invention therefore also involves the synthesis of the novel biocompatible thermoresponsive polymers. Specifically, the invention provides the synthesis of biocompatible amphiphilic co-polymers that are chain-extended and exhibit high water solubility just below body temperature, but are insoluble at 37° C. As a consequence of these characteristics, these polymers can act to stabilise colloidal particles under a first set of conditions, but aggregate the particles under a second set of conditions.

The surface-engineered microparticles with a biodegradable polymer core and a specifically-designed thermoresponsive biocompatible co-polymer corona can be produced in a simple one-pot procedure. The particles can form free-flowing suspensions below 37° C. but can reversibly form porous space-filling gels above this temperature as a result of chain collapse of the co-polymer corona. These particles can therefore be mixed with biological materials at less than 37° C., and then can form into stable encapsulating gels at body temperature; these stable encapsulating gels can support cell growth within the gel.

The combination of the ease of preparation, potential for scale-up, and the wide variations possible in the co-polymer corona layer due to controlled synthesis indicates that these systems are promising as a new class of biological delivery agent and support for tissue growth.

The present invention provides, inter alia, the smart particles, the process by which these materials can be produced and their use as cell support matrices.

SUMMARY OF INVENTION

The invention provides, in a first aspect, a method for the preparation of a polymer that displays a lower critical solution temperature, in aqueous media, that is between 10 to 90° C., the method comprising: the use of one or more monomer selected from polymerisable alkyleneglycol acrylate monomers and polymerisable alkyleneglycol methacrylate monomers as monomers in a polymerisation reaction.

A lower critical solution temperature may also be referred to as LCST or as an inverse-solubility temperature relationship. An LCST may be determined by heating at 1.0° C.min$^{-1}$ in a Beckman DU-640 spectrophotometer, with the LCST being taken as the temperature where there is the onset of a sharp increase in absorbance at 550 nm.

The method may involve the steps of:
  providing one or more monomer selected from polymerisable alkyleneglycol acrylate monomers and polymerisable alkyleneglycol methacrylate monomers; and
  carrying out polymerisation of the monomers to generate polymers with a lower critical solution temperatures, in aqueous media, of between 10 to 90° C.

Accordingly, of significance to the inventive step of the invention is the use of polymerisable alkyleneglycol acrylate and methacrylate monomers, either singly, or in various combinations, to generate polymers such that the lower critical solution temperatures in aqueous media are variant between 10-90° C.

The polymerisable alkyleneglycol acrylate monomers and polymerisable alkyleneglycol methacrylate monomers may be selected from: di(ethyleneglycol)-acrylate, oligo(ethyleneglycol)-acrylate, poly(ethyleneglycol)-acrylate, di(ethyleneglycol)-methacrylate, oligo(ethyleneglycol)-methacrylate, poly(ethyleneglycol)-methacrylate, poly(propyleneglycol)-acrylate, and poly(propyleneglycol)-methacrylate, either singly, or in various combinations.

In one embodiment, two monomers are used in combination, i.e. the polymer obtained is a copolymer. It may be, for example, that the method involves the polymerisation of poly(ethyleneglycol)methacrylate (PEGMA) and poly(propylene glycol) methacrylate (PPGMA). In one embodiment the PEGMA may have a Mn of about 475 and the PPGMA may have a Mn of about 430.

Any polymerisation technique can be used in the method of the invention to generate the polymer materials. Especially preferable are free-radical methods and controlled free-radical methods, including, but not exclusively, atom transfer radical polymerisation (ATRP).

The combinations of the monomer units in the generated polymer can be random, or can be controlled, such that sequence specific block-co-polymers are produced in any combination of monomers.

The choice of starting monomers (in particular their molar mass) and the polymerisation conditions can be controlled to vary the molar mass of the generated polymer. The molar masses of the generated polymers can be varied to be from 1 kDa up to over 1000 kDa. Preferably, for biomedical applications, the molar masses of the polymers are between 25-75 kDa with polydispersity (Mw/Mn) indices between 1-2.5.

The invention also provides, in a second aspect, a polymer that displays a lower critical solution temperature, in aqueous media, that is between 10 to 90° C., the polymer being obtainable by the method of the first aspect.

Accordingly, the invention provides a polymer that displays a lower critical solution temperature, in aqueous media, that is between 10 to 90° C., the polymer being the polymerisation product of one or more monomer selected from polymerisable alkyleneglycol acrylate monomers and polymerisable alkyleneglycol methacrylate monomers.

The polymers can be random, or can be controlled, sequence specific, block-co-polymers.

The polymers can have molar masses from 1 kDa up to over 1000 kDa. Preferably, for biomedical applications, the molar masses of the polymers are between 25-75 kDa with polydispersity (Mw/Mn) indices between 1-2.5.

The polymer may be the polymerisation product of one or more monomer selected from: di(ethyleneglycol)-acrylate, oligo(ethyleneglycol)-acrylate, poly(ethyleneglycol)-acrylate, di(ethyleneglycol)-methacrylate, oligo(ethyleneglycol)-methacrylate, poly(ethyleneglycol)-methacrylate, poly(propyleneglycol)-acrylate, and poly(propyleneglycol)-methacrylate, either singly, or in various combinations.

In one embodiment, the polymer is the polymerisation product of two monomers, i.e. it is a copolymer. It may be, for example, that the polymer is the polymerisation product of poly(ethyleneglycol)methacrylate (PEGMA) and poly(propylene glycol) methacrylate (PPGMA). In one embodiment the PEGMA may have a Mn of about 475 and the PPGMA may have a Mn of about 430. It may be that the PEGAM-PPGMA copolymer has a Mn of about 15,500.

The polymers of the invention may hereafter be referred to as LCST polymers.

The polymers are suitably biocompatible amphiphilic copolymers that are chain-extended and exhibit high water solubility just below body temperature, but are insoluble at 37° C. Thus these polymers can act to stabilise colloidal particles under a first set of conditions, but aggregate the particles under a second set of conditions.

Accordingly, the invention provides, in a third aspect, the use of the polymers of the second aspect, either singly or in combination, as surface-engineering surfactants during preparation of polymer particles by a method selected from emulsion methods, diffusion methods and evaporation methods.

Accordingly, the invention also provides, in a fourth aspect, a method for the preparation of polymer particles, the method comprising:
  the provision of one or more polymer in accordance with the second aspect; and
  the addition of the polymer, as surface-engineering surfactant, to a reaction mixture for the preparation of a polymer particle by a method selected from emulsion methods, diffusion methods and evaporation methods.

The invention also provides, in a fifth aspect, polymer particles obtainable by the method of the fourth aspect.

Accordingly, the invention provides polymer particles that are obtainable by a method selected from emulsion methods, diffusion methods and evaporation methods carried out in the presence of surface-engineering surfactant which is one or more polymer according to the second aspect.

The invention provides polymer particles that have a biodegradable polymer core and a thermoresponsive biocompatible co-polymer corona, wherein the co-polymer is a polymer according to the second aspect.

The polymer particles of the invention can have a bulk phase/core of any organic composition, but especially preferable are biodegradable polymers such as poly(lactic-co-glycolic acid) PLGA or its constituent homo-polymers. Accordingly, it is preferred that the polymer particles have a bulk phase/core of poly(lactic-co-glycolic acid), poly(lactic acid) or poly(glycolic acid).

The use of the LCST polymers during emulsion/diffusion/evaporation synthesis procedures with PLGA results in the formation of stable polymer particles varying between 100 nm to 100 µm diameter, with 500 nm to 5 µm being most preferable for biomedical applications.

Accordingly, in one embodiment there is provided polymer particles that have a bulk phase/core of PLGA and that are obtainable by a method selected from emulsion methods, diffusion methods and evaporation methods, carried out in the presence of surface-engineering surfactant which is one or more polymer according to the second aspect.

In one embodiment, the invention provides polymer particles that have a biodegradable polymer core and a thermoresponsive biocompatible co-polymer corona, wherein the biodegradable polymer core is PLGA and the co-polymer is the polymerisation product of PEGMA and PPGMA.

An aspect crucial to the inventive step is the ability of the LCST polymers to sterically stabilise the bulk polymer particles in aqueous media below their LCST, but to exhibit reduced stability above the LCST.

Accordingly, the polymer particles in accordance with the fifth aspect are surprisingly beneficial in that they are stable at a temperature below the LCST of the polymer of the second aspect, but they have reduced stability at temperatures above the LCST of the polymer of the second aspect. This change can be used as a trigger to associate/disassociate the LCST polymers and their combinations with the bulk polymer particles.

Although the invention is mainly described in relation to the use of a temperature change to evoke a change in the steric stabilisation properties of the LCST polymers, the LCST of a LCST polymer can vary with other properties of the solution in which the particles reside. For example, LCST can be affected by ionic strength, electric field, pH, solvent composition and any agents used as co-solvents. Any factor that changes the lower critical solution temperature of the LCST polymers can be varied to cause a change in the steric stabilisation properties of the LCST polymers and therefore cause a change in stability of the polymer particles of the fifth aspect.

Thus it can be envisaged that any change in solvent property, i.e. the ability of a liquid or liquid mixture to dissolve a solute, that affects lower critical solution temperature, can be used as a trigger to associate/disassociate the LCST polymers and their combinations with particles.

Thus the invention relates to polymer particles that can reversibly associate from solution/suspension and their application in the biomedical field.

The key applications for the invention are in controlled release, including flavour/fragrance release and especially in the biomedical field. The bulk of the polymer particles can incorporate actives, which for biomedical applications will be small molecule drugs and biopharmaceuticals for conventional drug delivery, or slow release growth factors and other soluble molecules for tissue growth, organ repair and regenerative medicine.

The polymer particles of the invention may therefore comprise active ingredients selected from: flavours, fragrances, small molecule drugs and biopharmaceuticals, and slow release growth factors and other soluble molecules for tissue growth, organ repair and regenerative medicine. These active ingredients are suitably incorporated in the bulk of the polymer particles.

In the worked examples the actives incorporated in the bulk of the particles are exemplified by fluorescent labels but for biomedical applications these would be small molecule drugs and biopharmaceuticals for conventional drug delivery, or slow release growth factors and other soluble molecules for tissue growth.

Accordingly, in a sixth aspect, the invention provides the use of the polymer particles of the fifth aspect in controlled release applications.

The applications, may, for example, be selected from flavour release applications, fragrance release applications and biomedical applications, such as conventional drug delivery applications. In particular, the applications may involve release of small molecule drugs or biopharmaceuticals for conventional drug delivery, or release of slow release growth factors and other soluble molecules for tissue growth, organ repair and regenerative medicine.

The particles may disperse with cells, or other biological materials, at temperatures below 37° C. to form free-flowing suspensions, and form space-filling gels at body temperature that support cell growth.

In a seventh aspect, therefore, the invention provides a product which comprises the polymer particles of the fifth aspect and biological material such as cells.

Such a product will be a dispersion below the lower critical solution temperature of the polymer of the second aspect. It may therefore be initially provided as a free flowing suspension.

Such a product can be used to encapsulate the cells or other biological material above the lower critical solution temperature of the polymer of the second aspect. At such a temperature it forms a space filling gel that supports the growth of the cell or other biological material.

Preferably, the lower critical solution temperature of the polymer of the second aspect is just below body temperature such that the product is a dispersion at room temperature and a gel at body temperature.

Essentially, when cells are provided together with the particles, the particles can form a porous cocoon for the cells during cell growth; this will allow the generation of matrix architectures that can promote cell-cell contact and foster enhanced tissue generation.

The polymer particles of the invention can be therefore be viewed as a colloidal cell delivery system.

The invention also provides, in an eighth aspect, the use of the polymer particles of the fifth aspect as cell support matrices.

The invention also provides, in a ninth aspect, a cell support matrix comprising the polymer particles of the fifth aspect.

The invention also provides, in a tenth aspect, a free flowing suspension comprising (i) cells and (ii) the polymer particles of the fifth aspect, at a temperature below 37° C.

The invention also provides, in an eleventh aspect, a space filling gel that supports cell growth comprising (i) cells and (ii) the polymer particles of the fifth aspect, at body temperature.

The invention also provides the use of polymers, of the second aspect, either singly or in combination, to prepare microparticles that disperse with cells at temperatures below 37° C. to form free-flowing suspensions, and that form space-filling gels at body temperature that support cell growth.

The invention also provides the use of polymers, of the second aspect, either singly or in combination, to partition into the surface of biodegradable polymer spheres during particle preparation, thus generating microparticles having highly controllable colloidal stability and biomaterial properties.

Figure 1:
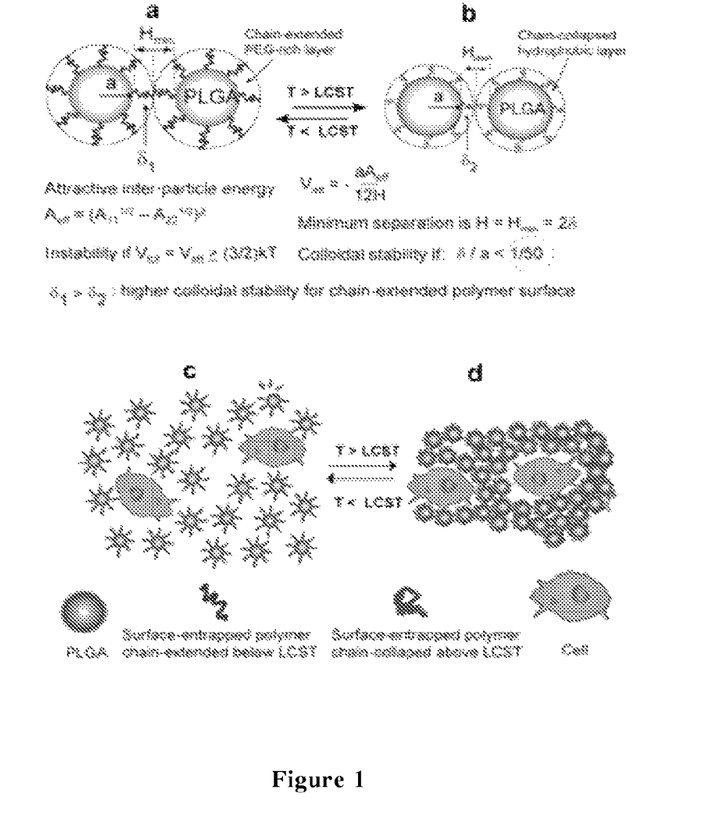
FIG. 1 is a schematic of the polymer particles of the invention, which can act as a colloidal cell delivery system

FIG. 1 provides an illustration of the concepts of the invention.

FIG. 1(a) shows the concept underlying steric stabilisation of microparticles; chain extension of a hydrated PEGMA-co-PPGMA corona prevents inter-particle attractive forces dominating. In FIG. 1(b) it can be seen that collapse of the PEGMA-co-PPGMA layer above the LCST reduces colloidal stability; attractive interactions between particles causes aggregation.

The extension of this concept to dispersions of particles and cells below LCST is shown in FIG. 1(c); encapsulation of cells occurs above the LCST as shown in FIG. 1(d).

In the present invention, surface-engineered smart particles are provided that are simple to prepare, exhibit well-controlled thermoresponsive behaviour, and are biocompatible and biodegradable. These materials offer a number of possibilities in cell delivery and tissue engineering applications.

For example, the surface chemistry of the LCST polymer could be controlled through modifications of co-monomers in the initial polymerisation to afford additional functionalities and responses that are biomimetic in nature. These could be acid-base responses to help regulate PLGA degradation, or bioadhesive functionalities to mimic key features of the extracellular matrix.

DESCRIPTION OF THE FIGURES

The non-limiting figures, which illustrate the invention, are as follows.

DETAILED DESCRIPTION OF THE INVENTION

Examples of the invention were prepared as follows.

Materials

The materials used were:

PLGA (lactide/glycolide molar ratio of 75/25, molecular weight Mn=12000, PDI=1.50) was purchased from AstraZeneca and used as supplied.

The polymer (surfactant-copolymer or LCST polymer) PEGMA-co-PPGMA (PEGMA/PPGMA=25:75, molecular weight Mn=15,500, PDI=1.61) was prepared via copolymerization of poly (ethylene glycol) methacrylate (PEGMA, Mn=475, Aldrich) and poly (propylene glycol) methacrylate (PPGMA, Mn=430, Aldrich), as described further below.

Ethyl acetate, azobisisobutyronitrile (AIBN) and 1-dodecanethiol were of analytical grade from Aldrich and used as supplied.

Copper(I) bromide (Aldrich, 98%) and copper(I) chloride (Acros, 95%) were washed with glacial acetic acid in order to remove any soluble oxidized species, filtered, washed with ethanol, and dried.

Methods

1. Preparation of LCST Copolymer: PEGMA-co-PPGMA a) Conventional Free Radical Polymerisation.

A round bottom flask fitted with a three-way stopcock was charged with AIBN (0.957 g, 6.1 mmole), PEGMA (5.532 g, 11.6 mmoles), PPGMA (15 g, 34.9 mmoles) and 1-dodecanethiol (0.38 g, 1.86 mmoles) in deoxygenated butanone (30 ml). The solution was stirred for 10 minutes until the contents were fully dissolved, then the contents were deoxygenated by freeze-thaw cycles (×3) followed by a nitrogen purge. The flask was immersed in an oil bath and polymerisation was conducted at 70° C. for 8 hours. The solution was diluted with acetone and precipitated into a large excess of hexane. After removal of the upper solvent layer, the precipitated polymer was dried in vacuo to get rid of the residual solvent. Then the polymer was dissolved in deionised water and subsequently purified by dialysis (molecular weight cut off: 6000) against fresh deionised water. Finally, water was removed by azeotropic distillation with ethanol to leave the amphiphilic co-polymer.

b) Atom Transfer Radical Polymerisation.

A round bottom flask fitted with a three-way stopcock was charged with CuBr (64.5 mg, 0.448 mmoles), bipyridine (139 mg, 0.891 mmoles), and then connected to either a nitrogen line or a vacuum pump. Oxygen was removed by repeated vacuum-nitrogen cycles. Once filled with nitrogen, the flask was filled with degassed PEGMA (5.532 g, 11.6 mmoles), PPGMA (15 g, 34.9 mmoles) and butanone (30 ml). After stirring for one hour at room temperature, methyl 2-bromopropionate solution (1.1 mL) in butanone (0.42M) was added, and the polymerisation was conducted at the desired temperature (typically 60° C.) for 10 hours. After polymerization, the solution was diluted with acetone and passed through a silica column to remove copper catalyst and precipitated into a large excess of hexane. Further purification was re-precipitations and dialysis followed by lyophilisation as described above.

2. Preparation of Dansyl-Copolymer PEGMA-co-PPGMA 1 g PEGMA-co-PPGMA (Mn=15,500) was dissolved in THF (15 ml). Triethylamine (0.0139 g, 0.137 mmoles) and dansyl chloride (0.037 g, 0.137 mmoles) was added to the solution. The reaction was then placed in the dark under stirring for overnight at room temperature. The reaction solution was filtered, and then added dropwise into hexane under vigorous stirring. The solution was then kept still for 30 minutes and the precipitated polymer sample was collected. The polymer was purified by precipitation three times and finally dried in vacuum oven at room temperature.

3. Preparation of PLGA Microparticles Coated with Copolymer PEGMA-co-PPGMA

Figure 2:
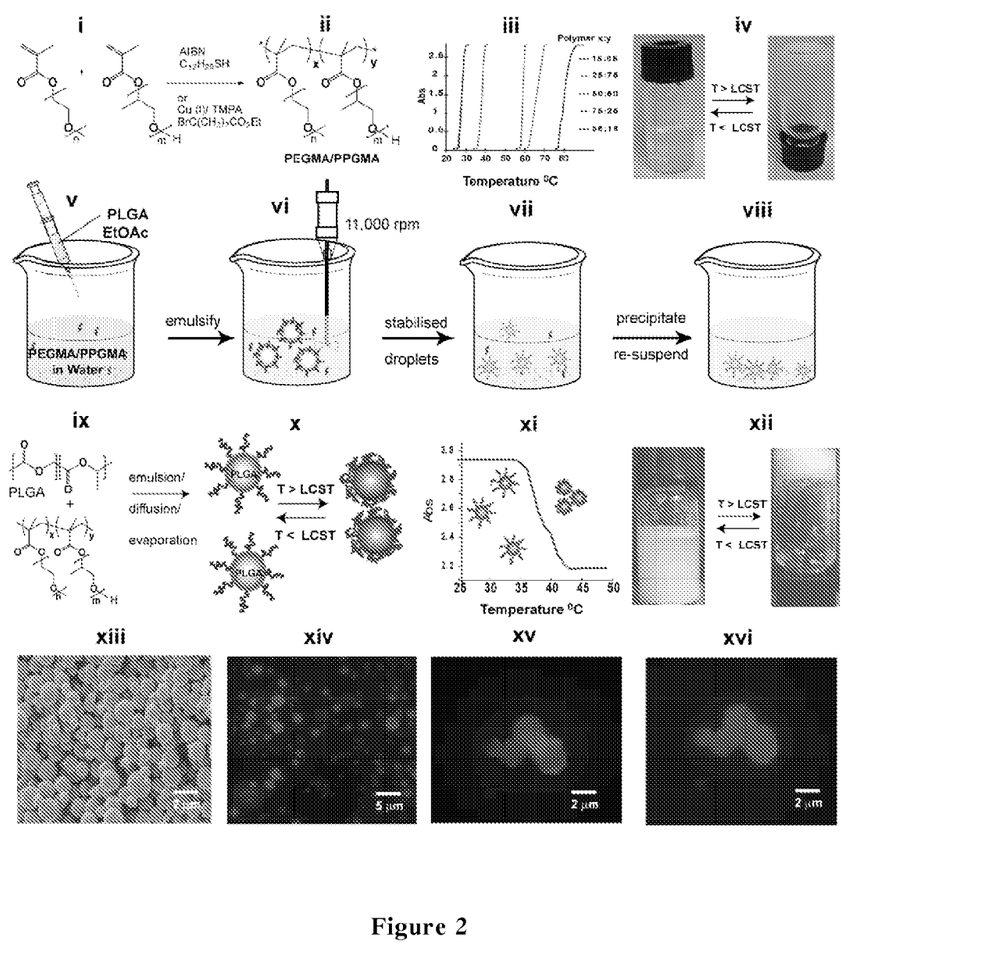
FIG. 2 illustrates the synthesis and properties of the polymer particles of the invention, which are thermoresponsive biodegradable microparticles

PLGA microparticles were prepared using an emulsion-evaporation-diffusion method (illustrated in FIG. 2). Typically, PLGA (200 mg) was dissolved in ethyl acetate (5 mL) and added to a solution of copolymer PEGMA-co-PPGMA in water (10 mL, 2 mg.mL−1). The resultant emulsion was homogenized at 11000 rpm for 45 seconds and added to a second PEGMA-co-PPGMA solution (15 ml, 2 mg.mL$^{-1}$) with further homogenization at 1100 rpm for 45 seconds. The organic solvent from the particle cores was removed in vacuo. Microparticles were separated by centrifugation (2500 rpm) from the aqueous phase, and re-suspended in water prior to lyophilisation.

Description of Analytical Techniques i. Determination of Lower Critical Solution Temperatures (LCST)

PEGMA-co-PPGMA polymer solutions in PBS (pH 7.4, 3 mg.mL-1) were heated at 1.0 0C.min−1 in a Beckman DU-640 spectrophotometer. The LCSTs of the copolymer systems were considered to be the onset of a sharp increase in absorbance at 550 nm.

ii. Gel Permeation Chromatography

Number average molecular weight (Mn), weight average molecular weight (Mw) and polydispersity (Mw/Mn) were obtained by Gel Permeation Chromatography (PL-120 and PL-50 Polymer Labs) with triple detection. The columns (30 cm PLgel Mixed-C, 2 in series) were eluted with THF and calibrated with polystyrene standards. All calibration and analysis were performed at 40° C. and a flow rate of 1 mL/min: under these conditions all of the products were fully dissolved in THF, and passed through 0.2 μm filter before injection with little or no backpressure observed.

iii. Particle Size Measurements

Micelle and microparticle sizes and distributions were measured using Malvern Zetasizer Nano and Coulter LS 230 (Beckman Coulter) instruments. For dynamic light scattering experiments, PEGMA-co-PPGMA solutions (1 mg.mL−1) were prepared in DI water and filtered prior to measurement using a 0.45 μm disposable filter (PTPE Acrodisc CR) in a 12.5×12.5 mm polystyrene disposable cuvette. For microparticle size measurements with the Coulter LS230, samples were re-suspended in DI water at an obscuration value between 8%-12%.

iv. Uniaxial Compression Tests

Uniaxial compression tests were conducted at ambient conditions with a Texture Analyser TA HDPlus supplied from Stable Micro Systems. Injectability was determined at 2 mm/sec through a 1 ml BD Plastipak™ syringe nozzle. Scaffold compression strength (wet and dry) was determined at 0.01 mm/sec following gel formation in the 4.5 mm diameter syringe barrel at 37° C. for 30 minutes.

Figure 7:
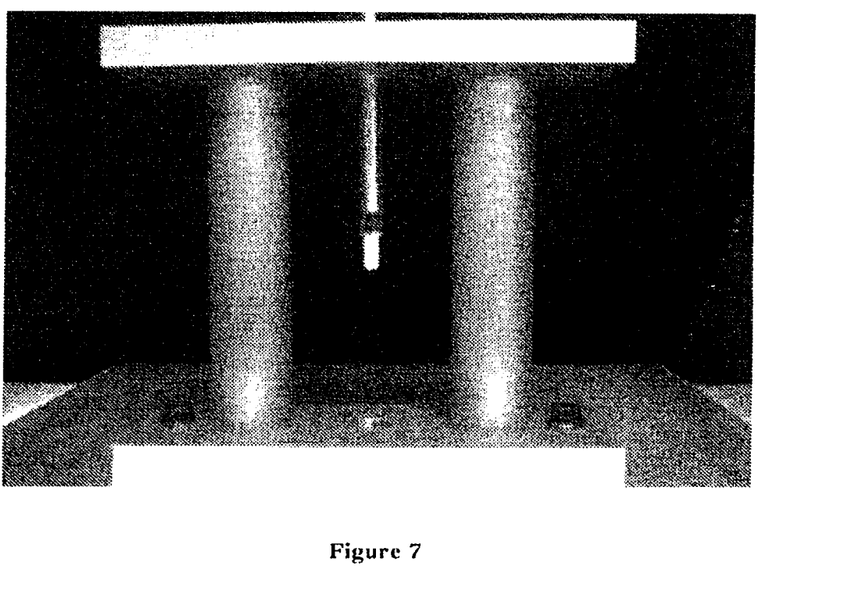
FIG. 7 shows the equipment used for uniaxial compression tests

FIG. 7 shows the apparatus used for the uniaxial compression tests.

v. Scanning Electron Microscopy

Scanning electron micrographs were recorded using a JEOL JSM-6060LV instrument. Polymer microparticles were placed on platinum stubs and sputter coated for 4 minutes, using a complex rotating planetary motion to allow irregular surfaces to be uniformly coated.

vi. Cell Culture

Cells from the C2C12 line were cultured in Dulbecco's modified Eagle's medium (DMEM), supplemented with 10% fetal bovine serum (FBS), 1% glutamine and 2.5 mg/mL amphotericin B (antibiotic/antimycotic solution), in a humidified incubator at 37° C. and 5% CO2. Cells were passaged every 2-3 days, using 0.25% trypsin/0.02% EDTA in PBS and reseeded prior to use. For microscopy experiments, PLGA microparticles were placed in Eppendorf vials and UV sterilized for 2 hours. C2C12 cells were trypsinised and re-suspended in DMEM, then centrifuged and re-suspended in DMEM containing fluorescent dye (C34551 Cell Tracker Orange CMRA) for 45 minutes. Then the labelled cells were centrifuged and added with Hank's Buffered Salt Solution (HBSS). Approximately 500000 cells (in 0.25 ml of HBSS buffer) were then mixed with PLGA microparticles (150 mg). The mixture were incubated in a non tissue culture six well plates at 37° C. for 30 minutes to form scaffold and followed adding DMEM to further incubation. Fluorescence images were taken after the cells were washed with sterile PBS and transferred to fresh non tissue culture six well plates. Cell viability was assessed using Alamar Blue assay (Biosource Europe).

Analysis

A. Characteristics for Copolymers of PEGMA and PPGMA

The new biocompatible responsive polymers synthesised by polymerisation of poly(ethyleneglycol)methacrylate (PEGMA) and poly(propylene glycol) methacrylate (PPGMA) in various monomer ratios, by the methods described above, are shown in Table 1.

TABLE 1

Polymerisation of PEGMA and PPGMA via Atom Transfer Radical Polymerisation (ATRP) and conventional free-radical polymerisation (FRP)

| [PEGMA]:[PPGMA]:[I]$^a$ or CTA$^b$ (mol ratio) | Mn | PDI | Yield | LCST (° C.) |
|---|---|---|---|---|
| 70:30:1 a | 33,500 | 1.43 | 80% | 70 |
| 50:50:1 a | 32,700 | 1.37 | 81% | 59 |
| 25:75:1 a | 31,700 | 1.33 | 79% | 36 |
| 25:75:2 a | 16,700 | 1.39 | 83% | 35 |
| 25:75:2 b | 30,300 | 1.69 | 99% | 34 |
| 25:75:4 b | 15,500 | 1.61 | 93% | 36 |

For ATRP: I$^a$=Initiator, [I]/[Cu(I)]/[Bipy]=2:1:2, Initiator: Methyl 2-bromopropionate, Monomer/Solvent (v/v)=1:1, Solvent: butanone. Reaction conditions: 60° C. for 10 hrs.
For FRP: AIBN was used as initiator, AIBN/monomer (weight ratio)=0.5%, monomer/solvent (v/v)=1:1. Solvent: butanone, reaction conditions: 70° C. for 8 hours.

Both conventional free-radical polymerisation (FRP) and atom transfer radical polymerisation (ATRP) routes can be used to generate comb co-polymers that exhibit lower critical solution temperatures (LCSTs) in phosphate buffered saline (PBS) at pH 7.4.

There is an interest in polymers that would exhibit LCST at body temperature. PEGMA25-PPGMA75 co-polymers of varying molar mass and polydispersity were successfully prepared with LCST around 37° C.

Control of the ratio of initiator: monomer in ATRP routes and of the ratio of chain transfer agent (CTA): monomer allows control over molar mass, whilst the co-monomer ratio enables tuning of the LCST over a wide temperature range.

Figure 5:
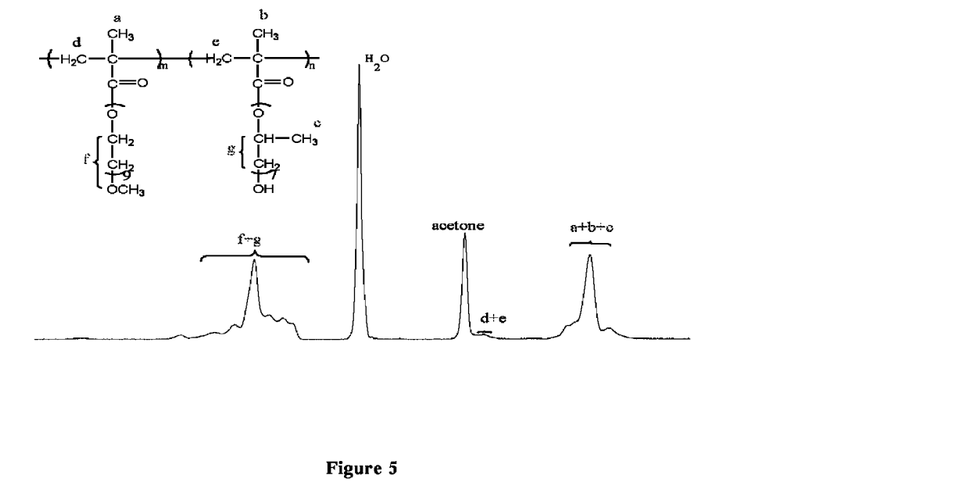
FIG. 5 shows an H NMR spectrum of the copolymer PEGMA-co-PPGMA (25/75), which is a LCST polymer of the invention

$^1$H NMR was carried out on the copolymer PEGMA-co-PPGMA (25/75), and the spectrum is shown in FIG. 5.

Figure 9:
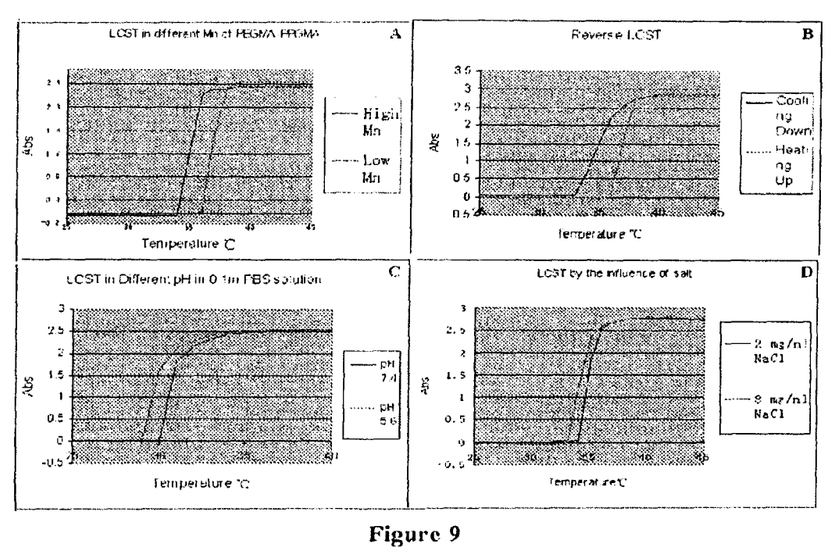
FIG. 9 shows characteristics of LCST polymers of the invention in different environments

The effect of molecular weight on the LCST of the polymers was assessed (using copolymers with the same monomeric components) and the results are shown in FIG. 9A. FIG. 9B shows the LCST for the copolymer PEGMA-co-PPGMA both heating up and cooling down. FIG. 9C shows the influence of pH on the LCST of the copolymer. FIG. 9D shows the effect of NaCl concentration on the LCST. In all figures, PEGMA-co-PPGMA (25/75) was used and the concentration of the copolymer was 3 mg/ml in each case.

The coil-to-globule phase transition for PEGMA$_x$PPGMA$_y$ co-polymers is shown via increased light-scattering in FIG. 2(iii). The phase transitions of the synthesised polymers are seen to be sharp.

Increases in ratios of hydrophilic PEGMA components to hydrophobic PPGMA monomer increased the LCST as expected (see both Table 1 and FIG. 2(iii)). However, and importantly for this application, the LCST was similar across a wide range of molar mass for a given PEGMA:PPGMA molar ratio.

FIG. 2(iv) depicts sol-to-gel transition for the LCST polymers. Low viscosity solutions were formed with PEGMA$_{25}$PPGMA$_{75}$ co-polymers of low-to-intermediate molar masses (<30 kDa) below LCST; these polymers precipitated from solution above LCST.

Increasing the molar mass of PEGMA$_{25}$PPGMA$_{75}$ to 160 kDa resulted in a stable gel in water above LCST. The sample below LCST is on the left and the sample above LCST on the right.

At concentrations of ~1 mg.mL−1 in water, PEGMA$_{25}$PPGMA$_{75}$ polymers formed micelles, as evidenced by dynamic light scattering, with changes in hydrodynamic radius from ~100 nm to 350 nm as temperature was increased from below LCST (~35° C.), to above LCST respectively.

Figure 10:
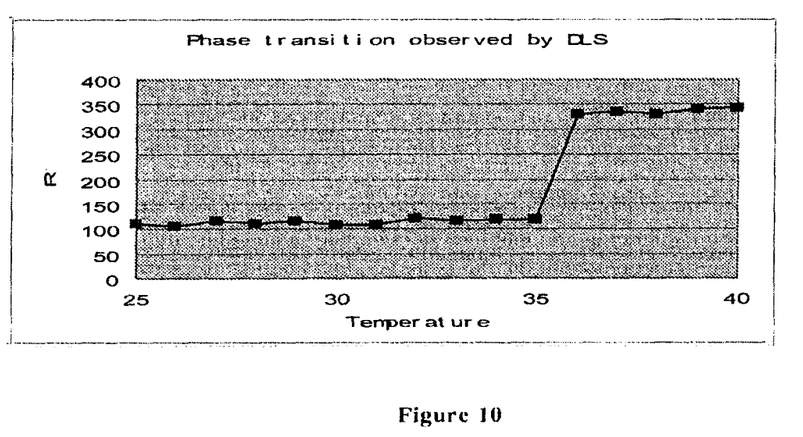
FIG. 10 shows the phase transition, as observed by DLS, for an aqueous solution of a copolymer PEGMA-PPGMA (25/75), which is a LCST polymer of the invention

FIG. 10 shows a plot of the hydrodynamic radius Rh (y axis) as a function of temperature (x axis, in ° C.) as measured by DLS for a aqueous solution (1 mg/ml) of the copolymer PEGMA-PPGMA (25/75).

B. Synthesis and Properties of Thermoresponsive Biodegradable Microparticles

In FIG. 2(i) there is an illustration of the monomers PEGMA and PPGMA which are co-polymerised via free-radical or controlled radical (ATRP) techniques to generate the comb co-polymers shown in FIG. 2(ii).

Preparation of surface-engineered smart particles is shown in FIG. 2(v-viii). Preparation of poly(lactic acid-co-glycolic acid) (PLGA) particles stabilised with PEGMA-PPGMA copolymers was carried out by an emulsion/diffusion/evaporation method. Specifically, a solution of PLGA in ethyl acetate is added to PEGMA-co-PPGMA polymer in water and stirred to generate an emulsion as shown in FIG. 2(v). The amphiphilic co-polymer stabilises the droplets of solvent containing PLGA during rapid stirring, as shown in FIG. 2(vi). Evaporation of solvent from the organic phase leaves PEGMA-coPPGMA-coated PLGA particles as shown in FIG. 2(vii). These are recovered by centrifugation and re-suspended in water, as shown in FIG. 2(viii).

A schematic of the surface response of PEGMA-co-PPGMA layer is shown in FIGS. 2(ix) and 2(x). It can be seen that the yielded microparticles have a 2-4 μm diameter with a surface 'corona' of the responsive LCST polymer.

The particles formed stable dispersions in water and PBS, but precipitated at low concentrations as shown by light scattering. FIG. 2(xi) shows the reduction in light-scattering that occurs as particles precipitate above the LCST.

When present in higher concentrations, the particles formed a hydrated free-standing gel. The formation of a space-filling gel (right) from a free-flowing suspension of the particles (left) upon a change in the temperature, to greater than the LCST, is shown in FIG. 2(xii).

Scanning Electron Microscopy confirmed particle morphology. SEM analysis of the particles is shown in FIG. 2(xiii). This indicates spherical particles of low polydispersity.

Encapsulation of Nile Red as a representative hydrophobic 'active' in the PLGA core enabled simple detection of the PLGA components, and selective filters in microscopy demonstrated presence both of the encapsulated dye and the surface-entrapped PEGMA-PPGMA layer.

The multi-layer structures of the coated particles were confirmed by fluorescence microscopy (Texas Red emission filter), with encapsulated Nile Red in the PLGA cores, as shown in FIG. 2(xiv).

The use of a dansyl-labelled PEGMA-PPGMA co-polymer allowed detection of the surface corona via fluorescence microscopy. The dansyl-labelled PEGMA-co-PPGMA revealed the surface coating, as shown in FIG. 2(xv) (DAPI emission filter), to be co-localized with the encapsulated Nile Red in the PLGA cores as shown in FIG. 2(xvi) (Texas Red emission filter).

Figure 6:
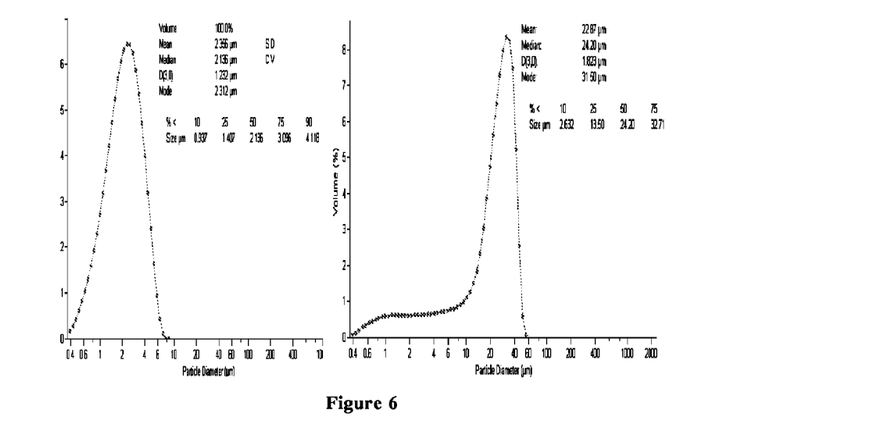
FIG. 6 illustrates the typical particle size of PLGA microparticles in accordance with the invention

FIG. 6 shows typical particle sizes for the PLGA microparticles of the invention.

Figure 11:
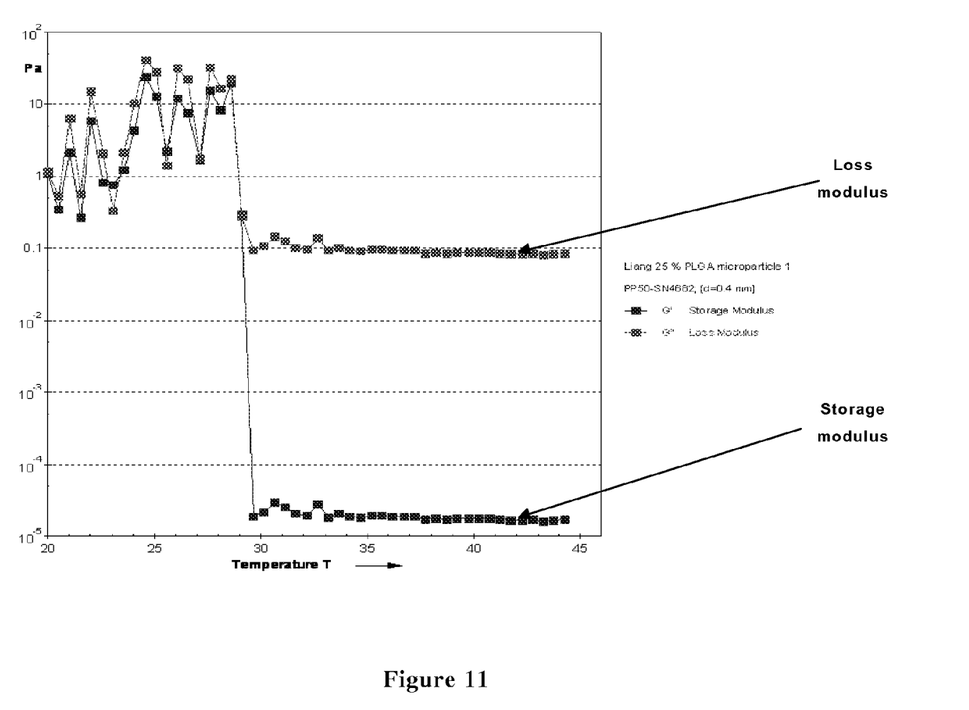
FIG. 11 shows rheology data for PLGA microparticles in accordance with the invention, from 20° C. to 45° C.

FIG. 11 shows rheology data for the PLGA microparticles (concentration of the PLGA microparticles, 25% w/v from 20° C. to 45° C.

Control of particle size was possible by variation of PEGMA-co-PPGMA:PLGA ratio with smaller beads and lower polydispersities resulting from higher ratios of PEGMA-co-PPGMA to PLGA. Typical preparations utilised PLGA:PEGMA-PPGMA ratio (w/w) of 2:1, yielding particles of 2.4 μm diameter, with a coefficient of variance of 63% and >90% of the particles with a diameter <5 μm. Similar particle sizes could be obtained at a PLGA:PEGMA-PPGMA ratio of 0.4:1, but increases in PLGA:PEGMA-co-PPGMA ratio beyond 4:1 increased particle size above 6 μm and led to subsequent aggregation.

The colloidal stability of the particles is dependent on the hydration shell of the PEGMA-co-PPGMA coating, which in turn varies with molar mass.

Thus, higher molar mass polymers are able to maintain colloidal stability of larger particles through a greater extension of the steric shielding layer as illustrated in FIG. 1.

C. Injectability and Mechanical Properties of Colloidal Suspensions and Thermoreversible Gels The injectability and mechanical properties of the colloidal suspensions and thermoreversible gels formed from the polymer particles were investigated with a texture analyser (FIG. 3).

The force required to inject suspensions of particles (60% w/v in PBS) is shown to vary only slightly compared to buffer and movement of the syringe barrel. This can be seen in FIG. 3a. The top line is the particle suspensions, the middle line is the movement of the syringe barrel, and the bottom line is the buffer.

The graph shows peak force of injection through a tapered 1.6 mm outlet nozzle for the empty syringe compared to buffer and 60% w/w solids scaffold suspension. The empty syringe requires a peak force of 1.17±0.15N, 1.125±0.18N with buffer and 2±0.03N with the particle suspension. The peak injectability force of the dispersion is well within the tolerances for the manual operation of the piston. The results for the 60% w/w solids show good repeatability within the timescales needed by a clinician.

Figure 3:
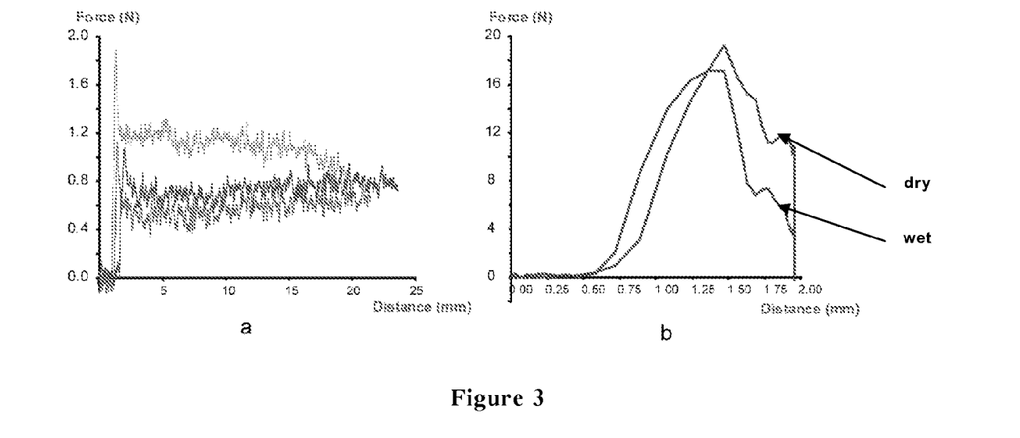
FIG. 3 shows texture probe analysis of colloidal suspensions and thermoreversible gels formed from the polymer particles of the invention

In FIG. 3b the force-distance curves of the wet and dry aggregated particles indicate a high strength gel.

The comparison of wet and dry gel strength following incubation at 37° C. for 30 minutes showed similar values at 17 and 19N respectively. It indicates that structure formation occurs within the incubation short incubation period.

D. In situ Encapsulation of Cells and Formation of Tissue Scaffold

Surface-engineered microparticles in accordance with the invention, prepared by the emulsion/diffusion/evaporation method as described above in method section 3, were mixed with C2C12 myoblasts as a model cell-line and formed free-flowing suspensions below the $PEGMA_{25}PPGMA_{75}$ LCST.

Figure 4:
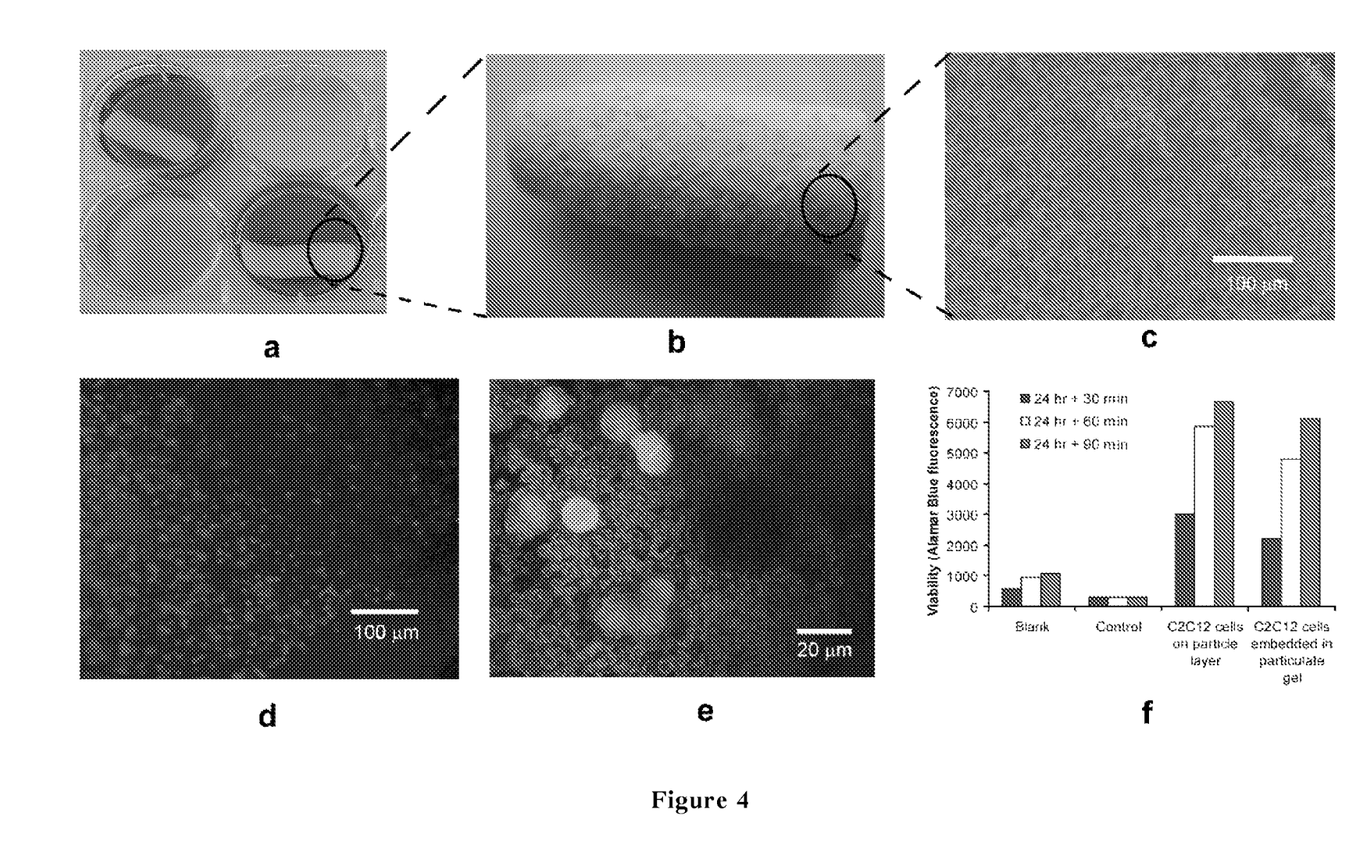
FIG. 4 shows in situ encapsulation of cells by polymer particles of the invention and formation of tissue scaffold from the polymer particles

Following dispersion of cells at room temperature with particles, encapsulation of cells takes place at 37° C., yielding stable gels. FIG. 4a shows these suspended in growth media. Accordingly, incubation of the mixed suspension of polymer particles and cells at 37° C. (i.e. above the lower critical solution temperature for the LCST polymer) generates gels, as for the polymer particles alone.

Micrographs of gels after 1 week incubation in DMEM are shown in FIGS. 4b and 4c. The porous nature of the gels was apparent in these SEM images and also from micro-computer tomography (μCT).

Figure 8:
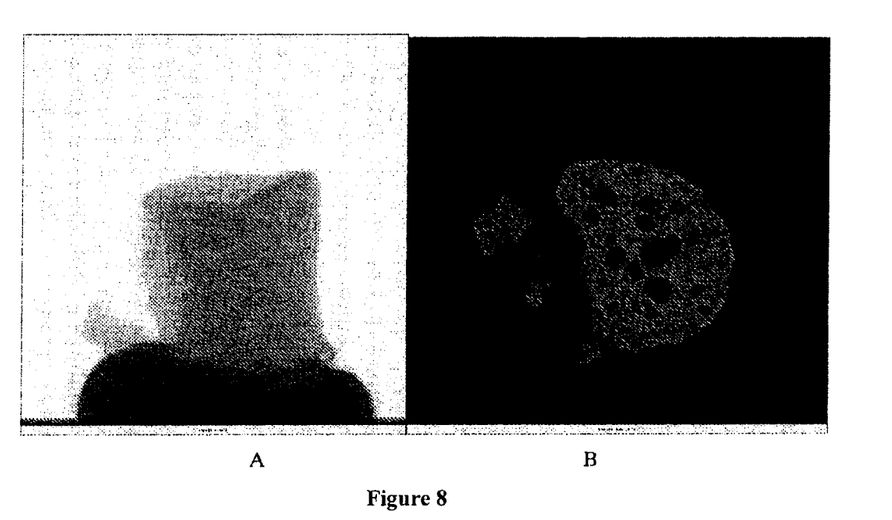
FIG. 8 shows A) spinning scan of MicroCT, B) reconstructure scan of MicroCT for the polymer particles of the invention

FIG. 8 shows the μCT images for the gels formed from the PLGA microparticles. FIG. 8A shows a μCT spinning scan and FIG. 8B shows a 3D reconstruction. These show macropores and cavities after cell encapsulation and drying.

Visualisation of cells within the porous matrix was carried out using Cell Tracker™ labelling; fluorescence microscopy indicated a homogeneous distribution of cells throughout the gel compared to control experiments on non-tissue culture plastic (FIG. 4d). This staining of the C2C12 cells with Cell Tracker™ in the sectioned PEGMA-PPGMA coated PLGA gel indicates enhanced cell viability in the gel.

Use of the Live/Dead™ stain indicated cell viability deep in the gel (FIG. 4e). Labelled C2C12 cells with Live/Dead™ stain are shown to fluoresce green while the matrix particles stain red.

The viability and metabolism was evaluated by the Alamar Blue assay. The data indicated that encapsulation of the cells via the in situ thermal gelation process took place with full retention of viability after 24 hrs, and that the cells were still growing at this timepoint. The Alamar Blue assay data is shown in FIG. 4f, confirming similar viability for cells in and on the gel matrix as compared to C2C12 cells on non-tissue culture plastic (Blank). The control sample is fluorescence from the PEGMA-PPGMA coated PLGA gel alone.

Significantly, the overall viability of the C2C12 cells was as good in the gels as it was for the same cells attached to the surface of a pre-formed PEGMA-co-PPGMA-PLGA matrix, thus indicating that cell growth could take place within the support with no barrier to ingress of nutrients over the initial time period.

The invention claimed is:

1. Polymer particles comprising:
at least one LCST polymer that displays a lower critical solution temperature, in aqueous media, that is between 10 to 90° C., the LCST polymer being the polymerisation product of one or more monomer selected from the group consisting of polymerisable alkyleneglycol acrylate monomers and polymerisable alkyleneglycol methacrylate monomers, wherein the polymer particles are obtainable by a method selected from at least one of an emulsion method, diffusion method and evaporation method carried out in the presence of said LCST polymer as a surface-engineering surfactant, and
wherein the polymer particles have a bulk phase or core of biodegradable polymers.

2. The polymer particles of claim 1 wherein the polymer particles further comprise, in their bulk phase or core, at least one active ingredient selected from the group consisting of: flavours, fragrances, small molecule drugs and biopharmaceuticals, and slow release growth factors and other soluble molecules for at least one of tissue growth, organ repair and regenerative medicine.

3. The polymer particles of claim 1 wherein the polymerisable alkyleneglycol acrylate monomers and polymerisable alkyleneglycol methacrylate monomers are selected from the group consisting of: di(ethyleneglycol)-acrylate, oligo(ethyleneglycol)-acrylate, poly(ethyleneglycol)-acrylate, di(ethyleneglycol)-methacrylate, oligo(ethyleneglycol)-methacrylate, poly(ethyleneglycol)-methacrylate, poly(propyleneglycol)-acrylate, and poly(propyleneglycol)-methacrylate.

4. The polymer particles of claim 1, wherein the LCST polymer that displays a lower critical solution temperature is the polymerisation product of two monomers.

5. The polymer particles of claim 4, wherein the two monomers are poly (ethyleneglycol)methacrylate (PEGMA) and poly (propylene glycol) methacrylate (PPGMA).

6. The polymer particles of claim 1, wherein the molar mass of the LCST polymer that displays a lower critical solution temperature is 25-75 kDa with a polydispersity (Mw/Mn) index of 1-2.5.

7. A product comprising the polymer particles as defined in claim 1 and a biological material.

8. The product of claim 7, wherein the biological material includes cells.

9. A cell support matrix comprising the polymer particles as defined in claim 1.

10. The cell support matrix of claim 9, wherein the polymer particles support cell growth.

11. A free flowing suspension comprising (i) cells and (ii) the polymer particles as defined in claim 1, at a temperature below 37° C.

12. A space filling gel that supports cell growth comprising (i) cells and (ii) the polymer particles as defined in claim 1, at body temperature.

13. Polymer particles comprising:
a biodegradable polymer core, and
a thermoresponsive biocompatible co-polymer corona, wherein the co-polymer is a LCST polymer that displays a lower critical solution temperature, in aqueous media, that is between 10 to 90° C., this LCST polymer being the polymerisation product of two or more monomers selected from the group consisting of polymerisable alkyleneglycol acrylate monomers and polymerisable alkyleneglycol methacrylate monomers.

14. The polymer particles of claim 13 wherein said LCST polymer is the polymerisation product of two monomers which are poly (ethyleneglycol)methacrylate (PEGMA) and poly (propylene glycol) methacrylate (PPGMA).

15. The polymer particles of claim 13 wherein the biodegradable polymer core comprises a biodegradable polymer selected from the group consisting of poly(lactic-co-glycolic acid), poly(lactic acid) and poly(glycolic acid).

16. The polymer particles of claim 13 wherein the biodegradable polymer core comprises at least one active ingredient selected from the group consisting of: flavours, fragrances, small molecule drugs and biopharmaceuticals, and slow release growth factors and other soluble molecules for at least one of tissue growth, organ repair and regenerative medicine.

17. The polymer particles of claim 13 wherein the molar mass of the LCST polymer that displays a lower critical solution temperature is 25-75 kDa with a polydispersity (Mw/Mn) index of 1-2.5.

18. Polymer particles comprising:
a biodegradable polymer core and
a thermoresponsive biocompatible co-polymer corona, wherein the co-polymer is a LCST polymer that displays a lower critical solution temperature, in aqueous media, that is between 10 to 90° C., the LCST polymer being a polymerisation product of poly (ethyleneglycol)methacrylate (PEGMA) and poly (propylene glycol) methacrylate (PPGMA).

19. The polymer particles of claim 18 wherein the biodegradable polymer core comprises a biodegradable polymer selected from the group consisting of ploy(lactic-co-glycolic acid), poly(lactic acid) and poly(glycolic acid).

20. The polymer particles of claim 18 wherein the biodegradable polymer core comprises at least one active ingredient selected from the group consisting of: flavours, fragrances, small molecule drugs and biopharmaceuticals, and slow release growth factors and other soluble molecules for at least one of tissue growth, organ repair and regenerative medicine.

21. The polymer particles of claim 18 wherein the molar mass of the LCST polymer that displays a lower critical solution temperature is 25-75 kDa with a polydispersity (Mw/Mn) index of 1-2.5.

* * * * *